(12) United States Patent (10) Patent No.: US 7,202,249 B2
Purandare (45) Date of Patent: Apr. 10, 2007

(54) ANTAGONISTS OF CHEMOKINE RECEPTORS

(75) Inventor: Ashok V. Purandare, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/648,677

(22) Filed: Aug. 25, 2003

(65) Prior Publication Data
US 2004/0048865 A1 Mar. 11, 2004

Related U.S. Application Data

(60) Provisional application No. 60/406,219, filed on Aug. 27, 2002.

(51) Int. Cl.
C07D 471/04 (2006.01)
A61K 31/519 (2006.01)
A61P 11/06 (2006.01)
A61P 19/02 (2006.01)
A61P 17/06 (2006.01)

(52) U.S. Cl. .................. 514/253.05; 544/279; 544/363; 514/264.1; 514/264.11

(58) Field of Classification Search .................... None
See application file for complete search history.

(56) References Cited

U.S. PATENT DOCUMENTS 6,245,332 B1   6/2001 Butcher et al.
6,313,292 B1 * 11/2001 Showalter et al. .......... 544/279

FOREIGN PATENT DOCUMENTS

WO   WO96/23068   8/1996
WO   WO01/79209   10/2001

OTHER PUBLICATIONS

Columbia University College of P & S Complete Home Medical Guide entry for Arthritis PREVENTION <http://cpmcnet.columbia.edu/texts/guide/hmg25_0006.html> downloaded from the Internet Mar. 5, 2003.*
The Medline Medical Encyclopedia entry for Psoriasis <http://www.nlm.nih.gov/medlineplus/ency/article/000434.htm> downloaded from the Internet Mar. 5, 2003 states that there is no known method to prevent it.*
The MDAdvice.com entry for Asthma <http://www.mdadvice.com/topics/asthma/info/1.htm> downloaded from the Internet Mar. 5, 2003.*
AllRefer.com Health entry for Chronic Obstructive Pulmonary Disease <http://health.allrefer.com/health/chronic-obstructive-pulmonary-disease-prevention.html> downloaded from the Internet Aug. 23, 2004.*

(Continued)

Primary Examiner—Mark L. Berch
(74) Attorney, Agent, or Firm—Laurelee A. Duncan

(57) ABSTRACT

Compounds are provided which are antagonists of chemokine receptor activity.

The compounds thereof have the structure

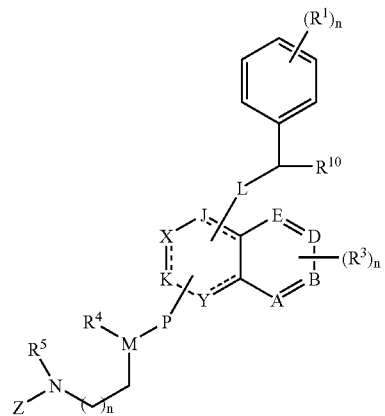

including enantiomers, diastereomers, tautomers, pharmaceutically acceptable salts and solvates thereof wherein:
A, B, D, E, X and Y are selected from N or C, J and K are C, and at least one of A, B, D, E, X and Y is N;
L is selected from O, NH and S, wherein L may be connected to any one of A, B, D, E, J, X, K or Y;
M is CH or N;
P is a bond or C=O, wherein P is connected to any one of J, X, K or Y;
Z is $C(=O)GR^2$ or $C(H)_2GR^2$; G is O or NH or none, or when Z is $C(=O)GR^2$, G also includes 1, 2 propylene;
n is 0–4;
$R^1$ is selected from halogen, —CN, —$CF_3$, substituted alkyl, aryl and heteroaryl;
$R^2$ is a heterocyclyl containing at least one N;
$R^3$ is selected from halogen, cyano, alkyl, substituted alkyl, aryl, substituted aryl, heteroaryl and substituted heteroaryl, wherein $R^3$ is connected to any one of A, B, D and E;
$R^4$ and $R^5$ are H;
or $R^4$ and $R^5$ may be taken together with the atoms to which they are attached to form a ring; and
$R^{10}$ is selected from H, alkyl, substituted alkyl, alkenyl, substituted alkenyl;
or E and $R^{10}$ may be taken together with the atoms to which they are attached to form a heteroaryl or heterocycloalkyl ring.

5 Claims, No Drawings

OTHER PUBLICATIONS

Allen et al, Bioorganic & Medicinal Chemistry Letters vol. 14, Issue 7, Apr. 2004, pp. 1619-1624.*
Barnes, Cytokine & Growth Factor Reviews vol. 14, Issue 6, Dec. 2003, pp. 511-522.*
Krueger, Journal of the American Academy of Dermatology 46(1), pp. 1-26 (2002).*
Barnes, Nature Reviews: Drug Discovery 4, 831 (2004).*
Lukas, "Role of Chemokines in the Pathogenesis of Asthma", Nature Reviews—Immunology, vol. 1, pp. 108-116, 2001.
Owen, "Chemokine Receptors in Airway Disease: Which Receptors to Target?", Pulmonary Pharmacology & Therapeutics, vol. 14, pp. 193-202, 2001.
Monteclaro et al., "Molecular Approaches to Identifying Ligand Binding and Signaling Domains of C-C Chemokine Receptors", Methods in Enzymology, vol. 288, pp. 70-84, 1997.
Saunders et al., "Opportunities for novel therapeutic agents acting at chemokine receptors", DDT vol. 4, No. 2, pp. 80-90, 1999.
Lopez et al., "TARC: novel mediator of allergic inflammation", Clinical & Experimental Allergy, vol. 31, pp. 1809-1812, 2001.
Campbell, J. J., et al., J. Immunol. 163: pp. 2353-2357 (1999).
Campbell, J. J., et al., Nature, 400: pp. 776-780 (1999).
Sallusto, F., et al., Eur. J. Immunol. 29: pp. 1617-1625 (1999).
Tang, H. L. et al., Science 284: pp. 819-822 (1999).
Krueger, J. G., J. Am. Acad. Dermatol 46: pp. 1-23 (2002).
Wakugawa M. et al., Drug News and Perspective 15(3): pp. 175-179 (2002).
Vestergaard et al., J. Clin. Invest. 104(8): pp. 1097-1105 (1999).
Vestergaard et al., J. Investigative Dermatology, 115: pp. 640-646 (2000).
Okazaki et al., Clin. Exp. Allergy; 32: pp. 1236-1242, 2002.
Lloyd et al., J. Exp. Med. 191 (2): pp. 265-273 (2000).
Ramos et al., Immunol. Rev. 177: pp. 31-42 (2000).
Lukacs et al., J. of Immunology 171(1): pp. 11-15 (2003).
Lloyd et al., Current Opin. In pharmacol 3: pp. 443-448 (2003).
Randolph, et al., J. Immunol. 162: pp. 2375-2383 (1999).
Jakubzick et al., Am. J. of Pathology, 165(4): pp. 1211-1221 (2204).
Gonzalo et al., J. Immunol., 163(1): pp. 403-411 (1999).
Schuh et al., FASEB J., 16(10): pp. 1313-1315 (2002).
Belperio et al., J. Immunol, 173(7): pp. 4692-4698 (2004).
Bordignon et al., J. Clin. Invest. 107(11): pp. 1357-1364 (2001).
Ruth et al., Arthritis Rheum, 44(5): pp. 2750-2760 (2001).
Thompson et al., J. Immunol. 166: pp. 6899-6906 (2001).
Biedermann et al., Eur. J. Immunol. 32(11): pp. 3171-3180 (2202).
Katschke et al., Arthritis and Rheum, 44(5): pp. 1022-1032 (2001).
Kawasaki et al., J. Immunology 166(3) pp. 2055-2062 (2001).
R. Malaviva, et al., Am J. Ther., 8(5) pp. 309-316, Sep.-Oct. 2001.
M. Daheshia, et al., Ann NY Acad Sci, 975, pp. 148-159, Dec. 2002.
W.R. Henderson, Jr., et al., Am. J. Respir Crit Care Med., 165(1), pp. 108-116, Sep. 1994.
T. T. Kung, et. al., Int. Arch Allegery Immunol., 105(1), pp. 83-90, Sep. 1994.
G. G. Brusselle, et al., Clin. Exp. Allergy, 24(1), pp. 73-80, Jan. 1994.
E. Hamelmann, et. al., Am. J. Respir. Crit. Care Med., 155(3), pp. 819-825, Mar. 1997.
S. J. Krinzman, et al., Am. J. Physiol., 271 (3 Pt 1):L pp. 476-483, Sep. 1996.

* cited by examiner

ANTAGONISTS OF CHEMOKINE RECEPTORS

This application claims the benefit of priority of U.S. Provisional Application Ser. No. 60/406,219, filed Aug. 27, 2002, the entirety of which is incorporated herein by reference.

FIELD OF THE INVENTION

The present invention relates to novel compounds which are antagonists of the chemokine receptors, and to methods of making such compounds. The invention also encompasses pharmaceutical compositions containing these compounds. The compounds and pharmaceutical compositions of the invention are particularly well suited as antagonists for the chemokine receptors and, consequently, can be advantageously used as therapeutic agents for the treatment of inflammatory, infectious, and immunoregulatory disorders and diseases, including asthma, COPD, and allergic diseases; rheumatoid arthritis, atherosclerosis, and psoriasis; solid organ transplant rejection, osteoarthritis, and inflammatory bowel syndrome. This invention also relates to methods for antagonizing chemokine receptors using the compounds of this invention alone or in combination with other pharmaceutically active agents.

BACKGROUND OF THE INVENTION

Chemokines are chemotactic cytokines that are released by a variety of cell types to attract and activate other cell types such as macrophages, T and B lymphocytes, basophils, neutrophils, mast cells, and eosinophils. They are broadly classified as C, CC, CXC, or $CX_3C$ chemokines dependent upon their amino acid sequence. For example, in CC chemokines the first two cysteines in the sequence are adjacent, while in CXC chemokines these cysteines are separated by one or more amino acid residues.

Chemokines bind to specific cell-surface receptors that belong to the family of G protein coupled seven transmembrane domain proteins. Upon ligand binding, chemokine receptors transduce an intracellular signal through the associated trimeric G proteins, resulting in calcium flux, changes in cell morphology, upregulated expression of cellular adhesion molecules, degranulation, and promotion of cell migration.

Chemokine receptors are implicated as key mediators of inflammatory, infectious, and immunoregulatory disorders and diseases, including asthma, COPD, and allergic diseases; rheumatoid arthritis, atherosclerosis, and psoriasis; solid organ transplant rejection, osteoarthritis, and inflammatory bowel syndrome. To illustrate, the CCR3 receptor appears to be a key mediator in attracting eosinophils and Th2 polarized CD4+ T cells to sites of inflammation in the lung, and also plays an important role in activating these cells. The ligands that bind CCR3 can induce a rapid increase in the intracellular calcium ion concentration (calcium flux), degranulation, increased expression of cell adhesion molecules, and cell migration. Agents that could modulate activity of the CCR13 receptor would have utility in the treatment of disorders and diseases in which eosinophils or Th2 CD4+ T cells appear to play a prominent role. A similar utility has been demonstrated using antibodies specific for the murine CCR3 chemokine receptor. Such antibodies can be used to deplete eosinophils in in vivo inflammatory models in mice.

Several mammalian viruses such as, but not limited to, cytomegaloviruses, herpesviruses, and poxviruses have been shown to express proteins with the binding properties of chemokine receptors in infected cells. In addition, several chemokine receptors have been demonstrated to act as cellular receptors for a variety of viruses, as well as some bacteria, and parasites. Thus, agents which modulate chemokine receptor activity may also have utility in infectious diseases. Examples would include, but not be limited to, blocking of HIV infection of CCR3, CCR5, or CXCR4 expressing cells; or in the prevention of manipulation of the immune response by viruses such as cytomegaloviruses that use a chemokine receptor for cellular infection.

CCR4 is a chemokine receptor that partners with the ligands MDC (macrophage derived chemokine) and TARC (thymus and activation-regulated chemokine), both of which are members of the beta or CC class of chemokines. The CCR4 chemokine receptor is important in facilitating the migration of selected CD4+ thymocytes to the thymus, and through the compartments of the thymus, as a part of the process of T cell education and differentiation. A CCR4 antagonist is expected to prevent recruitment of CD4+ Th2 polarized T cells to sites of inflammation by blocking chemotaxis and cellular activation. No known CCR4 specific antagonists are in the clinic at this time.

In vivo studies have demonstrated the potential of CCR4 as a therapeutic target. Treatment with antibodies specific for either TARC or MDC is effective in blocking allergic airway inflammation and hyperresponsiveness in mice. Antibodies to TARC are also effective in a bacteria-induced fulminant hepatic liver failure model in mice; a result thought to be due to a reduction in liver injury as mediated by T cells recruited by granuloma-derived TARC. Splenocytes and thymocytes isolated from CCR4-/- mice are unable to migrate in response to TARC or MDC. CCR4-/- mice exhibit significantly decreased mortality on administration of bacterial lipopolysaccharide. Blocking antibody to CCR4 is efficacious in reducing LPS toxicity in mice. Blocking antibody was also efficacious in reducing skin homing of CD4+ Th2 T cells.

CCR4 antagonists are expected to have therapeutic potential in the treatment of diseases such as asthma, rheumatoid arthritis, and psoriasis. Asthma is a chronic inflammatory disease of the airways with an estimated prevalence of 48 million patients in the US, Europe, and Japan. Children and juveniles represent 30% of these patients. Current therapies provide both acute relief of signs and symptoms (beta agonists, xanthines) and chronic disease maintenance (inhaled steroids, leukotriene antagonists). Many of these therapies are inhaled and have significant systemic side effect issues (particularly steroids). Leukotriene antagonists are dosed orally and have a better safety/tolerability profile, but with reduced efficacy compared to steroids. There is a significant need for better oral non-steroidal anti-inflammatory therapies to treat asthma.

Rheumatoid arthritis (RA) is a chronic autoimmune inflammatory disease and treatment for RA is aimed at relieving symptoms (analgesics, NSAIDS, steroids) and delaying disease progression (DMARDs). The rapid growth in this market has come from the introduction of new disease modifying agents, primarily biologics, which have improved efficacy and a unique adverse event profile. Although broader ranges of therapeutic options are now available, they are still insufficient to achieve optimal clinical control and there is a significant need for effective and well-tolerated oral medicines for routine maintenance therapy.

Psoriasis is a chronic skin disease and current therapies for psoriasis consist of topicals, UV therapy and potent systemics. Topicals are difficult to use and are not highly efficacious for moderate-to-severe disease. Moderate-to-severe patients (44%) are generally treated with uv therapy and/or systemics. UV therapy is inconvenient and carries the potential risk of skin cancer. Systemics such as cyclosporin or methotrexate come with significant side effects, including kidney and liver toxicity. Biologics are emerging therapies with varying degrees of efficacy. They are well tolerated and safer than current systemics, but require infusion or injection. A significant unmet need exists for a more effective and better-tolerated orally active medicine, particularly with the potential for use in maintenance therapy to prevent flares. An ideal therapy could be used for both clearance and maintenance.

The WO 02/30357 and 02/30358 patent application describes compounds and methods for modulating CCR4 function.

U.S. Pat. No. 6,245,332 is directed to methods for manipulating adhesion triggering and CCR4 mediated chemotaxis to affect the localization of T cells in targeted tissues. In one embodiment of the invention, the active agent is a CCR4 antagonist, that acts to enhance T cell localization. In another embodiment, the agent is an antagonist that blocks $cCR^4$ biological activity.

The WO 98/27815 patent application is directed to aminoquinolines which are useful as modulators ochemokine receptor activity. In particular, the compounds of the invention are useful as modulators of the chemokine receptors CCR-1, CCR-2, CCR-2A, CCR-2B, CCR-3, CCR-4, CCR-5, CXCR-3 and/or CXCR-4.

The WO 98/25605 patent application is directed to spiro-substituted azacycles which are useful as modulators of chemokine receptor activity. In particular, the compounds of the invention are useful as modulators of the chemokine receptors CCR-1, CCR-2, CCR-2A, CCR-2B, CCR-3, CCR-4, CCR-5, CXCR-3 and/or CXCR-4.

The WO 99/37617 patent application is directed to a method of treating a subject with a disease associated with aberrant leukocyte recruitment and/or activation. The method comprises administering to the subject a therapeutically effective amount of a compound of the invention.

The WO 01/79209 patent application relates to diazafluorenone derivatives which are IL-8 receptor antagonists and to methods of treating a chemokine-mediated disease in a mammal, including a human. According to this application, chemokine-mediated disease include psoriasis, atopic dermatitis, disease associated with pathological angiogenesis (i.e., cancer), asthma, chronic obstructive pulmonary disease, adult respiratory distress syndrome, arthritis, inflammatory bowel disease, Crohn's disease, ulcerative dolitis, gastric ulcer, spetic shock, endotoxic shock, gram-negative sepsis, toxic shock syndrome, stroke, atherosclerosis, cardiac and renal reperfusion injury, glomerulonephritis, thrombosis, Alzheimer's disease, graft versus host reaction or allograft rejections in a mammal, including a human.

There remains a need for potent selective antagonists of CCR4 chemokine receptors with improved pharmacological properties, physical properties and fewer side effects. Such inhibitors would have therapeutic potential in the treatment of asthma, rheumatoid arthritis and psoriasis. The compounds of the present invention are effective antagonists of the CCR4 chemokine receptor.

SUMMARY OF THE INVENTION

It is an object of the present invention to provide compounds of the following formula (I),

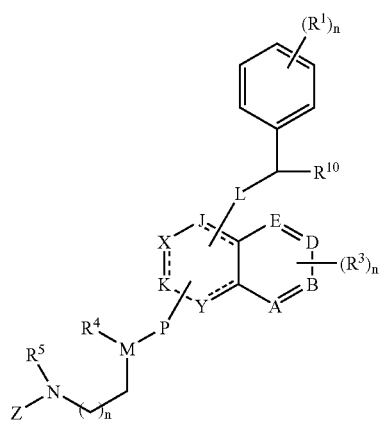

including enantiomers, diastereomers, tautomers, pharmaceutically acceptable salts and solvates thereof wherein:

A, B, D, E, X and Y are selected from N or C, J and K are C, and at least one of A, B, D, E, X and Y is N;

L is selected from O, NH and S, wherein L may be connected to any one of A, B, D, E, J, X, K or Y;

M is CH or N;

P is a bond or C=O, wherein P is connected to any one of J, X, K or Y;

Z is $C(=O)GR^2$ or $C(H)_2GR^2$; G is O or NH or none, or when Z is $C(=O)GR^2$, G also includes 1, 2 propylene;

n is 0–4;

$R^1$ is selected from halogen, —CN, —$CF_3$, substituted alkyl, aryl and heteroaryl;

$R^2$ is a heterocyclyl containing at least one N;

$R^3$ is selected from halogen, cyano, alkyl, substituted alkyl, aryl, substituted aryl, heteroaryl and substituted heteroaryl, wherein $R^3$ is connected to any one of A, B, D and E;

$R^4$ and $R^5$ are H;

or $R^4$ and $R^5$ may be taken together with the atoms to which they are attached to form a ring; and $R^{10}$ is selected from H, alkyl, substituted alkyl, alkenyl, substituted alkenyl;

or E and $R^{10}$ may be taken together with the atoms to which they are attached to form a heteroaryl or heterocycloalkyl ring.

It is another object of the present invention to provide pharmaceutical compositions containing the chemokine receptor antagonist compounds of the invention.

It is yet another object of the present invention to provide methods for the treatment of CCR4 chemokine receptor associated disorders and the treatment or prevention of asthma, rheumatoid arthritis, psoriasis, solid organ transplant rejection or chronic obstructive pulmonary disease.

DETAILED DESCRIPTION OF THE INVENTION

[1] Thus in a first embodiment, the present invention provides a compound of formula (I)

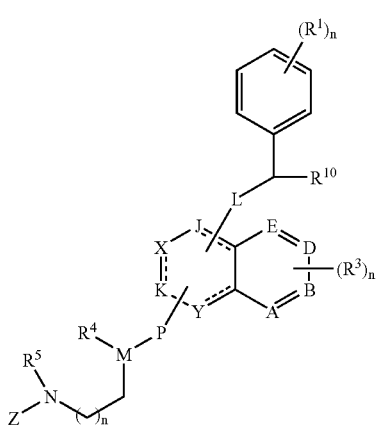

including enantiomers, diastereomers, tautomers, pharmaceutically acceptable salts and solvates thereof wherein the variables are defined as follows:

A, B, D, E, X and Y are selected from N or C, J and K are C, and at least one of A, B, D, E, X and Y is N;

L is selected from O, NH and S, wherein L may be connected to any one of A, B, D, E, J, X, K or Y;

M is CH or N;

P is a bond or C=O, wherein P is connected to any one of J, X, K or Y;

Z is C(=O)GR$^2$ or C(H)$_2$GR$^2$; G is O or NH or none, or when Z is C(=O)GR$^2$, G also includes 1,2 propylene;

n is 0–4;

R$^1$ is selected from halogen, —CN, —CF$_3$, substituted alkyl, aryl and heteroaryl;

R$^2$ is a heterocyclyl containing at least one N;

R$^3$ is selected from halogen, cyano, alkyl, substituted alkyl, aryl, substituted aryl, heteroaryl and substituted heteroaryl, wherein R$^3$ is connected to any one of A, B, D and E;

R$^4$ and R$^5$ are H;

or R$^4$ and R$^5$ may be taken together with the atoms to which they are attached to form a ring; and R$^{10}$ is selected from H, alkyl, substituted alkyl, alkenyl, substituted alkenyl;

or E and R$^{10}$ may be taken together with the atoms to which they are attached to form a heteroaryl or heterocycloalkyl ring.

[2] In a preferred embodiment, the present invention provides a compound of formula (I) including enantiomers, diastereomers, tautomers, pharmaceutically acceptable salts and solvates thereof wherein at least one of the following variables and preferably all are defined as follows:

A is N;
B, D and E are C;
Either of X or Y or both are N;
L is NH;
M is N;
n is 1;
R$^1$ is selected from halogen, —CN, —CF$_3$, substituted alkyl, aryl and heteroaryl;
R$^2$ is a heterocyclyl containing at least one N; and
R$^{10}$ is H.

Within the scope of this embodiment, there are two alternative embodiments that are particularly preferred. In the first particularly preferred embodiment at least one of the following variables and preferably all are defined as follows:

L is connected to J;
P is a bond; and
P is connected to K.

In the second particularly preferred embodiment at least one of the following variables and preferably all are defined as follows:

L is connected to D; and
P is connected to J.

[3] In another preferred embodiment, the present invention provides a compound of formula (I) including isomers, enantiomers, diastereomers, tautomers, pharmaceutically acceptable salts and solvates thereof selected from:

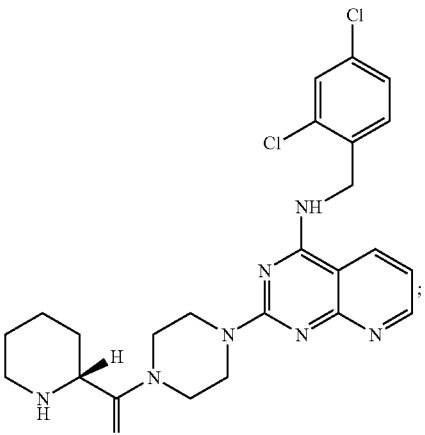

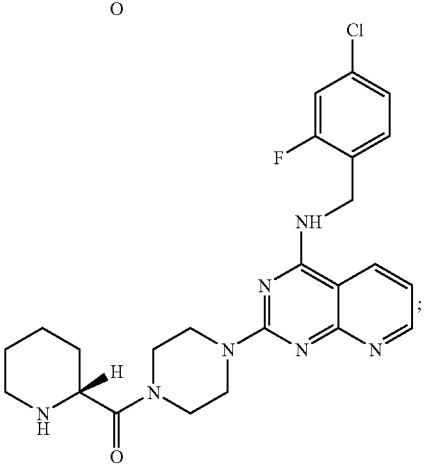

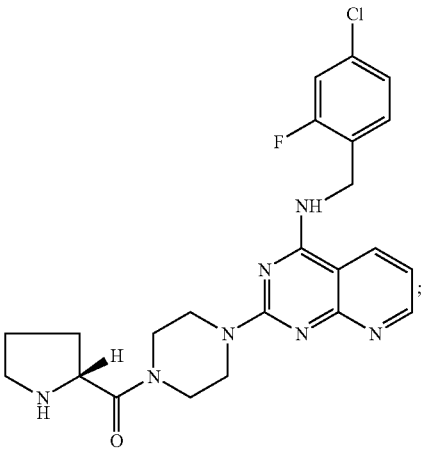

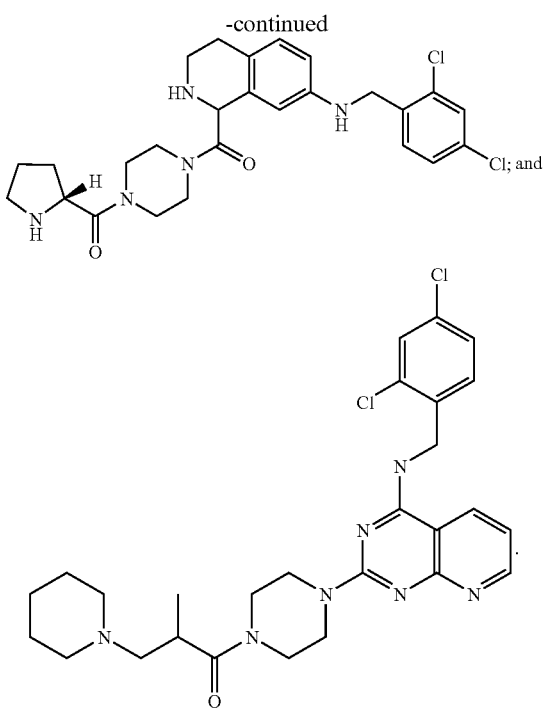

[4] In a second preferred embodiment, the present invention provides a pharmaceutical composition comprising: a compound of the invention and a pharmaceutically acceptable carrier.

[5] In third preferred embodiment, the present invention provides a method for the treatment of CCR4-mediated conditions or diseases comprising: administering a therapeutically effective amount of the pharmaceutical composition of the invention.

[6] In another preferred embodiment, the present invention provides a method for the treatment or prevention of asthma comprising: administering a therapeutically effective amount of the pharmaceutical composition of the invention.

[7] In another preferred embodiment, the present invention provides a method for the treatment or prevention of rheumatoid arthritis comprising: administering a therapeutically effective amount of the pharmaceutical composition of the invention.

[8] In another preferred embodiment, the present invention provides a method for the treatment or prevention of psoriasis comprising: administering a therapeutically effective amount of the pharmaceutical composition of the invention.

[9] In another preferred embodiment, the present invention provides a method for the treatment or prevention of solid organ transplant rejection comprising: administering a therapeutically effective amount of the pharmaceutical composition of the invention.

[10] In another preferred embodiment, the present invention provides a method for the treatment or prevention of chronic obstructure pulmonary disease comprising: administering a therapeutically effective amount of the pharmaceutical composition of the invention.

The following are definitions of the terms as used throughout this specification and claims. The initial definition provided for a group or term herein applies to that group or term throughout the present specification, individually or as part of another group, unless otherwise indicated.

The term "alkyl" refers to straight or branched chain hydrocarbon groups having 1 to 12 carbons atoms, preferably 1 to 8 carbon atoms, and most preferably 1 to 4 carbon atoms.

The term "substituted alkyl" refers to an alkyl group as defined above having one, two, or three substituents selected from the group consisting of halo, cyano, O—$R^7$, S—$R^7$, $NR^8R^9$, nitro, cycloalkyl, substituted cycloalkyl, oxo, aryl, substituted aryl, heterocycloalkyl, heteroaryl, $CO_2R^7$, $S(O)R^7$, $SO_2R^7$, $SO_3R^7$, $SO_2NR^8R^9$, $C(O)NR^8R^9$, C(O)alkyl, and C(O)H.

The term "alkenyl" refers to straight or branched chain hydrocarbon groups having 2 to 12 carbon atoms and one, two or three double bonds, preferably 2 to 6 carbon atoms and one double bond.

The term "substituted alkenyl" refers to an alkenyl group as defined above having one, two, or three substituents selected from the group consisting of halo, cyano, O—$R^7$, S—$R^7$, $NR^8R^9$, nitro, cycloalkyl, substituted cycloalkyl, oxo, aryl, substituted aryl, heterocycloalkyl, heteroaryl, $CO_2R^7$, $S(O)R^7$, $SO_2R^7$, $SO_3R^7$, $SO_2NR^8R^9$, $C(O)NR^8R^9$, C(O)alkyl, and C(O)H.

The term "alkynyl" refers to straight or branched chain hydrocarbon group having 2 to 12 carbon atoms and one, two or three triple bonds, preferably 2 to 6 carbon atoms and one triple bond.

The term "substituted alkynyl" refers to an alkynyl group as defined above having one, two or three substituents selected from the group consisting of halo, cyano, O—$R^7$, S—$R^7$, $NR^8R^9$, nitro, cycloalkyl, substituted cycloalkyl, oxo, aryl, substituted aryl, heterocycloalkyl, heteroaryl, $CO_2R^7$, $S(O)R^7$, $SO_2R^7$, $SO_3R^7$, $SO_2NR^8R^9$, $C(O)NR^8R^9$, C(O)alkyl, and C(O)H.

The term "halo" refers to chloro, bromo, fluoro, and iodo.

The term "cycloalkyl" refers to fully saturated and partially unsaturated monocyclic hydrocarbon rings of 3 to 9, preferably 3 to 7 carbon atoms. Also included in this definition are bicyclic rings where the cycloalkyl ring as defined above has a fused aryl, substituted aryl, cycloalkyl, substituted cycloalkyl, heterocycloalkyl, or heteroaryl ring provided that the point of attachment is in the cycloalkyl ring, i.e.

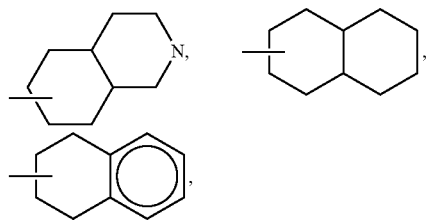

etc., as well as a cycloalkyl ring as defined above having a two or three carbon bridge or a spirocycloalkyl in which a carbon atom of the cycloallkyl ring has a carbon atom in common with a second cycloalkyl, substituted cycloalkyl, or heterocycloalkyl ring again provided that the point of attachment is in the cycloalkyl ring, i.e.

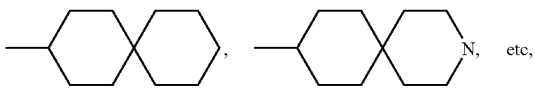

The term "substituted cycloalkyl" refers to such cycloalkyl group as defined above having one, two or three substituents selected from the group consisting of halogen, nitro, alkyl, substituted alkyl, alkenyl, cyano, cycloalkyl, substituted cycloalkyl, aryl, substituted aryl, heterocycloalkyl, heteroaryl, oxo, $OR^7$, $CO_2R^7$, $C(O)NR^8R^9$, $OC(O)R^7$, $OC(O)OR^7$, $OC(O)NR^8R^9$, $OCH_2CO_2R^7$, $C(O)R^7$, $NR^8R^9$, $NR^{10}C(O)R^7$, $NR^{10}C(O)OR^7$, $NR^{10}C(O)C(O)OR^7$, $NR^{10}C(O)C(O)NR^8R$, $NR^{10}C(O)C(O)$alkyl, $NR^{10}C(NCN)OR^7$, $NR^{10}C(O)NR^8R^9$, $NR^{10}(NCN)NR^8R^9$, $NR^{10}C(NR^{11})NR^8R^9$, $NR^{10}SO_2NR^8R^9$, $NR SO_2R^7$, $SR^7$, $S(O)R^7$, $SO_2R^7$, $SO_3R^7$, $SO_2NR^8R^9$, $NHOR^7$, $NR^{10}NR^8R^9$, $N(COR^7)OR^{10}$, $N(CO_2R^7)OR^{10}$, $C(O)NR^{10}(CR^{12}R^{13})_rR^7$, $CO(CR^{12}R^{13})_pO(CR^{14}R^{15})_qCO_2R_7$, $CO(CR^{12}R^{13})_rOR^7$, $CO(CR^{12}R^{13})_pO(CR^{14}R^{15})_qR^7$, $CO(CR^{12}R^{13})_rNR^8R^9$, $OC(O)O(CR^{12}R^{13})_mNR^8R^9$, $OC(O)N(CR^{12}R^{13})_rR^7$, $O(CR^{12}R^{13})_mNR^8R^9$, $NR^{10}C(O)(CR^{12}R^{13})_rR^7$, $NR^{10}C(O)(CR^{12}R^{13})_rOR^7$, $NR^{10}C(=NC)(CR^{12}R^{13})_rR^7$, $NR^{10}CO(CR^{12}R^{13})_rNR^8R^9$, $NR^{10}(CR^{12}R^{13})_mOR^7$, $NR^{10}(CR^{12}R^{13})_rCO_2R_7$, $NR^{10}(CR^{12}R^{13})_mNR^8R^9$, $NR^{10}(CR^{12}R^{13})_nSO_2(CR^{14}R^{15})_qR^7$, $CONR_{10}(CR^{12}R^{13})_nSO_2(CR^{14}R^{15})_qR^7$, $SO_2NR^{10}(CR^{12}R^{13})_nCO(CR^{14}R^{15})_qR^7$, and $SO_2NR^{10}(CR^{12}R^{13})_mOR^7$.

The term "aryl" refers to the phenyl, 1-naphthyl, and 2-naphthyl, preferably phenyl, as well as an aryl ring having a fused cycloalkyl, substituted cycloalkyl, heterocycloalkyl, or heteroaryl ring provided that the point of attachment is in the aryl ring, i.e.

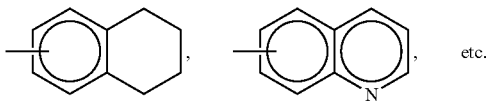

The term "substituted aryl" refers to such aryl groups as defined above having one, two, or three substituents selected from the group consisting of halogen, nitro, alkyl, substituted alkyl, alkenyl, cyano, cycloalkyl, substituted cycloalkyl, aryl, substituted aryl, heterocycloalkyl, heteroaryl, $OR^7$, $CO_2R^7 OC(O)NR^8R^9$, $OC(O)R^7$, $OC(O)OR^7$, $OC(O)NR^8R^9$, $OCH_2CO_2R^7$, $C(O)R^7$, $NR^8R^9$, $NR^{10}C(O)R^7$, $NR^{10}C(O)O R^7$, $NR^{10}C(O)C(O)OR^7$, $NR^{10}C(O)C(O)NR^8R^9$, $NR^{10}C(O)C(O)$alkyl, $NR^{10}C(NCN)OR^7$, $NR^{10}C(O)NR^8R^9$, $NR^{10}C(NCN)NR^8R^9$, $NR^{10}C(NR^{11})NR^8R^9$, $NR^{10}SO_2NR^8R^9$, $NR^{10}SO_2R^7$, $SR^7$, $S(O)R^7$, $SO_2R^7$, $SO_3R^7$, $SO_2NR^8R^9$, $NHOR^7$, $NR^{10}NR^8R^9$, $N(COR^7)OR^{10}$, $N(CO_2R^7)OR^{10}$, $C(O)NR^{10}(CR^{12}R^{13})_rR^7$, $CO(CR^{12}R^{13})_pO(CR^{14}R^{15})_qCO_2R_7$, $CO(CR^{12}R^{13})_rOR^7$, $CO(CR^{12}R^{13})_pO(CR^{14}R^{15})_qR^7$, $CO(CR^{12}R^{13})_rNR^8R^9$, $OC(O)O(CR^{12}R^{13})_mNR^8R^9$, $OC(O)N(CR^{12}R^{13})_rR^7$, $O(CR^{12}R^{13})_mNR^8R^9$, $NR^{10}C(O)(CR^{12}R^{13})_rR^7$, $NR^{10}C(O)(CR^{12}R^{13})_rOR^7$, $NR^{10}C(=NC)(CR^{12}R^{13})_rR^7$, $NR^{10}CO(CR^{12}R^{13})_rNR^8R^9$, $NR^{10}(CR^{12}R^{13})_mOR^7$, $NR^{10}(CR^{12}R^{13})_rCO_2R_7$, $NR^{10}(CR^{12}R^{13})_mNR^8R^9$, $NR^{10}(CR^{12}R^{13})_nSO_2(CR^{14}R^{15})_qR^7$, $R^7CONR^{10}(CR^{12}R^{13})_nSO_2(CR^{14}R^{15})_qR^7$, $SO_2NR^{10}(CR^{12}R^{13})_nCO(CR^{14}R^{15})_qR^7$, and $SO_2NR^{10}(CR^{12}R^{13})_mOR^7$ as well as pentafluorophenyl.

The term "substituted monocyclic ring system of 5 or 6 carbon atoms" refers to one, two or three substituents selected from the group consisting of halogen, nitro, alkyl, substituted alkyl, alkenyl, cyano, oxo, $OR^7$, cycloalkyl, substituted cycloalkyl, aryl, substituted aryl, heterocycloalkyl, heteroaryl, $CO_2R^7$, $C(O)NR^8R^9$, $OC(O)R^7$, $OC(O)OR^7$, $OC(O)NR^8R^9$, $OCH_2CO_2R^7$, $C(O)R^7$, $NR^8R^9$, $NR^{10}C(O)R^7$, $NR^{10}C(O)OR^7$, $NR^{10}C(O)C(O)OR^7$, $NR^{10}C(O)C(O)NR^8R^9$, $NR^{10}C(O)C(O)$alkyl, $NR^{10}C(NCN)OR^7$, $NR^{10}C(O)NR^8R^9$, $NR^{10}C(NCN)NR^8R^9$, $NR^{10}C(NR^{11})NR^8R^9$, $NR^{10}SO_2NR^8R^9$, $NR^{10}SO_2R^7$, $SR^7$, $S(O)R^7$, $SO_2R^7$, $SO_3R^7$, $SO_2NR^8R^9$, $NHOR^7$, $NR^{10}NR^8R^9$, $N(COR^7)OR^{10}$, $N(CO_2R^7)OR^{10}$, $C(O)NR^{10}(CR^{12}R^{13})_rR^7$, $CO(CR^{12}R^{13})_pO(CR^{14}R^{15})_qCO_2R_7$, $CO(CR^{12}R^{13})_rOR^7$, $CO(CR^{12}R^{13})_pO(CR^{14}R^{15})_qR^7$, $CO(CR^{12}R^{13})_rNR^8R^9$, $OC(O)O(CR^{12}R^{13})_mNR^8R^9$, $OC(O)N(CR^{12}R^{13})_rR^7$, $O(CR^{12}R^{13})_mNR^8R^9$, $NR^{10}C(O)(CR^{12}R^{13})_rR^7$, $NR^{10}C(O)(CR^{12}R^{13})_rOR^7$, $NR^{10}C(=NC)(CR^{12}R^{13})_rR^7$, $NR^{10}CO(CR^{12}R^{13})_rNR^8R^9$, $NR^{10}(CR^{12}R^{13})_mOR^7$, $NR^{10}(CR^{12}R^{13})_rCO_2R_7$, $NR^{10}(CR^{12}R^{13})_mNR^8R^9$, $NR^{10}(CR^{12}R^{13})_nSO_2(CR^{14}R^{15})_qR^7$, $CONR_{10}(CR^{12}R^{13})_nSO_2(CR^{14}R^{15})_qR^7$, $SO_2NR^{10}(CR^{12}R^{13})_nCO(CR^{14}R^{15})_qR^7$, and $SO_2NR^{10}(CR^{12}R^{13})_mOR^7$.

The term "heterocycloalkyl", refers to substituted and unsubstituted saturated or partially saturated monocyclic rings of 3 to 7 members and bicyclic rings of 7 to 11 members having one or two O or S atoms and/or one to four N atoms provided that the total number of heteroatoms is four or less and that the heterocycloalkyl ring contains at least one carbon atom. The nitrogen and sulfur atoms may optionally be oxidized, and the nitrogen atoms may optionally be quaternized. The bicyclic heterocycloalkyl ring may also contain a two or three carbon bridge between available carbon or nitrogen atoms. The bicyclic heterocycloalkyl rings may also have a cycloalkyl, substituted cycloalkyl, aryl, substituted aryl, heterocycloalkyl, or heteroaryl ring fused to the monocyclic ring provided that the point of attachment is through an available carbon or nitrogen atom of the heterocycloalkyl ring. Also included are spiroheterocycloalkyl rings wherein a carbon atom of the heterocycloalkyl ring is in common with a second heterocycloalkyl ring, a cycloalkyl ring, or a substituted cycloalkyl ring again provided that the point of attachment is through an available carbon or nitrogen atom of the heterocycloalkyl ring. The heterocycloalkyl ring can have one, two or three substituents on available carbon or nitrogen atoms selected from the group consisting of halogen, nitro, alkyl, substituted alkyl, alkenyl, cyano, cycloalkyl, substituted cycloalkyl, aryl, substituted aryl, heterocycloalkyl, heteroaryl, oxo, $OR^7$, $CO_2R^7$, $C(O)NR^8R^9$, $OC(O)R^7$, $OC(O)OR^7$, $OC(O)NR^8R^9$, $OCH_2CO_2R^7$, $C(O)R^7$, $NR^8R^9$, $NR^{10}C(O)R^7$, $NR^{10}C(O)OR^7$, $NR^{10}C(O)C(O)OR^7$, $NR^{10}C(O)C(O)NR^8R^9$, $NR^{10}C(O)C(O)$alkyl, $NR^{10}C(NCN)OR^7$, $NR^{10}C(O)NR^8R^9$, $NR^{10}C(NCN)NR^8R^9$, $NR^{10}C(NR^{11})NR^8R^9$, $NR^{10}SO_2NR^8R^9$, $NR^{10}SO_2R^7$, $SR^7$, $S(O)R^7 SO_2R^7$, $SO_3R^7 SO_2NR^8R^9$, $NHOR^7$, $NR^8ONR^8R^9$, $N(COR^7)OR^{10}$, $N(CO_2R^7)OR^{10}$, $C(O)NR^{10}(CR^{12}R^{13})_rR^7$, $CO(CR^{12}R^{13})_pO(CR^{14}R^{15})_qCO_2R^7$, $CO(CR^{12}R^{13})_rOR^7$, $CO(CR^{12}R^{13})_pO(CR^{14}R^{15})_qR^7$, $CO(CR^{12}R^{13})_rNR^8R^9$, $OC(O)O(CR^{12}R^{13})_mNR^8R^9$, $OC(O)N(CR^{12}R^{13})_rR^7$, $O(CR^{12}R^{13})_mNR^8R^9$, $NR^{10}C(O)(CR^{12}R^{13})_rR^7$, $NR^{10}C(O)(CR^{12}R^{13})_rOR^7 NR^{10}C(=NC)(CR^{12}R^{13})_rR^7$, $NR^{10}CO(CR^{12}R^{13})_rNR^8R^9$, $NR^{10}(CR^{12}R^{13})_mOR^7$, $NR^{10}(CR^{12}R^{13})_rCO_2R_7$, $NR^{10}(CR^{12}R^{13})_mNR^8R^9$, $NR^{10}(CR^{12}R^{13})_nSO_2(CR^{14}R^{15})_qR^7$, $CONR_{10}(CR^{12}R^{13})_nSO_2(CR^{14}R^{15})_qR^7$, $SO_2NR^{10}(CR^{12}R^{13})_nCO(CR^{14}R^{15})_qR^7$, and $SO_2NR^{10}(CR^{12}R^{13})_mOR^7$.

Exemplary monocyclic heterocycloalkyl groups include pyrrolidinyl, pyrrolinyl, pyrazolinyl, pyrazolidinyl, oxetanyl, imidazolinyl, imidazolidinyl, oxazolidinyl, isothiazolidinyl, isoxazolinyl, thiazolidinyl, tetrahydrofuryl, piperidinyl, piperazinyl, tetrahydrothiopyranyl, tetrahydropyranyl, morpholinyl, thiamorpholinyl, thiamorpholinyl sulfoxide, thiamorpholinyl sulfone, tetrahydrothiopyranylsulfone, 1,3-dioxolanyl, tetrahydro-1,1-dioxothienyl, dioxanyl, thietanyl, thiiranyl, triazolinyl, triazolidinyl, etc.

Exemplary bicyclic heterocycloalkyl groups include indolinyl, quinuclidinyl, tetrahydroisoquinolinyl, benzimidazolinyl, chromanyl, dihydrobenzofuran, dihydrofuro[3,4-b]pyridinyl, dihydroisoindolyl, dihydroquinazolinyl (such as 3,4-dihydro-4-oxo-quinazolinyl), benzofurazanyl, benzotriazolinyl, dihydrobenzofuryl, dihydrobenzothienyl, dihydrobenzothiopyranyl, dihydrobenzothiopyranyl sulfone, dihydrobenzopyranyl, isoindolinyl, isochromanyl, benzodioxolyl, tetrahydroquinolinyl, etc.

Exemplary spirocyclic heterocycloalkyl groups include 1-aza[4.5]spirodecane, 2-aza[4.5]spirodecane, 1-aza[5.5]spiroundecane, 2-aza[5.5]spiroundecane, 3-aza[5.5]spiroundecane, etc.

The term "heteroaryl" refers to substituted and unsubstituted aromatic 5 or 6 membered monocyclic groups and 9 or 10 membered bicyclic groups which have at least one heteroatom (O, S or N) in at least one of rings. Each ring of the heteroaryl groups containing a heteroatom can contain one or two O and S atoms and/or from one to four N atoms provided that the total number of heteroatoms in each ring is four or less. The bicyclic heteroaryl rings are formed by fusing a cycloalkyl, substituted cycloalkyl, aryl, substituted aryl, heterocycloalkyl, or heteroaryl group to the monocyclic heteroaryl ring as defined above. The heteroaryl group is attached via an available carbon or nitrogen in the aromatic heteroaryl ring. The nitrogen and sulfur atoms may optionally be oxidized and the nitrogen atoms may optionally be quaternized. The heteroaryl ring system may be substituted at an available carbon or nitrogen by one, two, or three substituents selected from the group consisting of halogen, nitro, alkyl, substituted alkyl, alkenyl, cyano, cycloalkyl, substituted cycloalkyl, aryl, substituted aryl, heterocycloalkyl, heteroaryl, $OR^7$, $CO_2R^7$, $C(O)NR^8R^9OC(O)R^7$, $OC(O)OR^7$, $OC(O)NR^8R^9$, $OCH_2CO_2R^7$, $C(O)R^7$, $NR^8R^9$, $NR^{10}C(O)R^7$, $NR^{10}C(O)OR^7$, $NR^{10}C(O)C(O)OR^7$, $NR^{10}C(O)C(O)NR^8R^9$, $NR^{10}C(O)C(O)$ alkyl, $NR^{10}C(NCN)OR^7$, $NR^{10}C(O)NR^8R^9$, $NR^{10}C(NCN)NR^8R^9$, $NR^{10}C(NR^{11})NR^8R^9$, $NR^{10}SO_2NR^8R^9$, $NR^{10}SO_2R^7$, $SR^7$, $S(O)R^7$, $SO_2R^7$, $SO_3R^7$, $SO_2NR^8R^9$, $NHOR^7$, $NR^{10}NR^8R^9$, $N(COR^7)OR^{10}$, $N(CO_2R^7)OR^{10}$, $C(O)NR^{10}(CR^{12}R^{13})_rR^7$, $CO(CR^{12}R^{13})_pO(CR^{14}R^{15})_qCO_2R_7$, $CO(CR^{12}R^{13})_pOR^7$, $CO(CR^{12}R^{13})_pO(CR^{14}R^{15})_qR^7$, $CO(CR^{12}R^{13})_rNR^8R^9$, $OC(O)O(CR^{12}R^{13})_mNR^8R^9$, $OC(O)N(CR^{12}R^{13})_rR^7$, $O(CR^{12}R^{13})_mNR^8R^9$, $NR^{10}C(O)(CR^{12}R^{13})_rR^7$, $NR^{10}C(O)(CR^{12}R^{13})_rOR^7$, $NR^{10}C(=NC)(CR^{12}R^{13})_rR^7$, $NR^{10}CO(CR^{12}R^{13})_rNR^8R^9$, $NR^{10}(CR^{12}R^{13})_mOR^7$, $NR^{10}(CR^{12}R^{13})_rCO_2R_7$, $NR^{10}(CR^{12}R^{13})_mNR^8R^9$, $NR^{10}(CR^{12}R^{13})_nSO_2(CR^{14}R^{15})_qR^7$, $CONR^{10}(CR^{12}R^{13})_nSO_2(CR^{14}R^{15})_qR^7$, $SO_2NR^{10}(CR^{12}R^{13})_nCO(CR^{14}R^{15})_qR^7$, and $SO_2NR^{10}(CR^{12}R^{13})_mOR^7$.

Exemplary monocyclic heteroaryl groups include pyrrolyl, pyrazolyl, imidazolyl, oxazolyl, isoxazolyl, thiazolyl, thiadiazolyl, isothiazolyl, pyridinyl, furyl, thienyl, oxadiazolyl, 2-oxazepinyl, azepinyl, pyrazinyl, pyrimidinyl, pyridazinyl, triazinyl, triazolyl, etc. Exemplary bicyclic heteroaryl groups include benzothiazolyl, benzoxazolyl, benzothienyl, benzofuryl, quinolinyl, quinolinyl-N-oxide, isoquinolinyl, benzimidazolyl, benzopyranyl, indolizinyl, cinnolinyl, quinoxalinyl, indazolyl, pyrrolopyridyl, furopyridinyl (such as furo [2,3-c]pyridinyl, furo[3,1-b]pyridinyl or furo[2,3-b]pyridinyl), benzisothiazolyl, benzisoxazolyl, benzodiazinyl, benzothiopyranyl, benzotriazolyl, benzpyrazolyl, naphthyridinyl, phthalazinyl, purinyl, pyridopyridyl, quinazolinyl, thienofuryl, thienopyridyl, thienothienyl, etc.

As used herein, the phrase "CCR4-mediated condition or disease" and related phrases and terms refer to a condition or disease characterized by inappropriate, e.g., less than or greater than normal, CCR4 functional activity. Inappropriate CCR4 functional activity might arise as the result of CCR4 expression in cells which normal do not express CR4, increased CCR4 expression (leading to e.g., inflammatory and immunoregulatory disorders and diseases) or decreased CCR4 expression. A CCR4-mediated condition or disease may be completely or partially mediated by inappropriate CCR4 functional activity. However, a CCR4-mediated condition or disease is one in which modulation of CCR4 results in some effect on the underlying condition or disease (e.g., a CCR4 antagonist results in some improvement in patient well-being in at least some patients).

Diseases and conditions associated with inflammation, infection and cancer can be treated or prevented with the compounds and compositions of the present invention. Diseases and conditions mediated by CCR4 include contact hypersensitivity, atopic dermatitis, allergic airway hypersensitivity, atherosclerosis, diseases of innate immunity (e.g., septic shock) and diseases or conditions caused by platelet aggregation or thrombosis. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as arthritis (including rheumatoid and psoriatic), multiple sclerosis, systemic lupus erythematosus, type I diabetes, glomerulonephritis, and the like, (10) graft rejection (including allograft rejection and graft-v-host disease), and (11) other diseases in which undesired inflammatory responses are to be inhibited (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout.

As used herein the term "treating" includes prophylactic and therapeutic uses, and refers to the alleviation of symptoms of a particular disorder in a patient, the improvement of an ascertainable measurement associated with a particular disorder, or the prevention of a particular immune response (such as transplant rejection). The term "patient" refers to a mammal, preferably a human.

The compounds of this invention may contain one or more asymmetric carbon atoms and thus may occur as racemates and racemic mixtures, single enantiomers, diastereomeric mixtures and individual diastereomers. All such isomers of the compounds disclosed herein are expressly included within the scope of the present invention. Each stereogenic carbon may be of the R or S configuration.

Combinations of substituents and variables thereof that result in stable compounds are also contemplated within the present invention. The term "stable" as used herein refers to compounds which possess stability sufficient to allow manufacture and which maintain their integrity for a sufficient period of time to be useful as a therapeutic or diagnostic agent.

As used herein, the compounds of this invention are defined to include pharmaceutically acceptable derivatives and prodrugs thereof. A "pharmaceutically acceptable derivative or prodrug" includes any pharmaceutically acceptable salt, ester, salt of an ester, or other derivative of a compound of the present invention which, upon administration to a subject, is capable of providing (directly or indirectly) a compound of the invention. Particularly favored derivatives and prodrugs are those that increase the bioavailability of the compounds of the present invention when such compound is administered to a subject (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to a compound of the present invention.

Pharmaceutically acceptable salts of the compounds disclosed herein include those derived from pharmaceutically acceptable inorganic and organic acids and bases known to those skilled in the art. Examples of suitable acid salts include, but are not limited to, the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, trifluoroacetic, tosylate and undecanoate. Other acids, for example oxalic, while not in themselves pharmaceutically acceptable, may be employed in the preparation of salts useful as intermediates in obtaining the compounds of the present invention and their pharmaceutically acceptable acid additional salts.

Salts derived from appropriate bases include, but are not limited to, the following: alkali metal (e.g., sodium), alkaline earth metal (e.g., magnesium), ammonium and N—($C_{1-4}$ alkyl)$_4$+ salts. The present invention also envisions the quaternization of any basic nitrogen-containing groups of the compounds disclosed herein. Water- or oil-soluble or dispersible products may be obtained by such quaternization.

Methods of Preparation

The compounds of the present invention may be synthesized using conventional techniques known in the art. Advantageously, these compounds are conveniently synthesized from readily available starting materials. Following are general synthetic schemes for manufacturing compounds of the present invention. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence or order to give the desired compound(s). All documents cited herein are incorporated herein by reference in their entirety.

Compounds of the present invention can be made by many methods, which will be known to one skilled in the art of organic chemistry. In general, the time taken to complete a reaction procedure will be judged by the person performing the procedure, preferably with the aid of information obtained by monitoring the reaction by methods such as HPLC or TLC. A reaction does not have to go to completion to be useful to this invention. The preparation of heterocycles useful to this invention are described in the series of books: "Comprehensive Heterocyclic Chemistry, The Structure, Reactions, Synthesis and Uses, of Heterocyclic Compounds" Katritzky, A. R., Rees, C. W. Eds Pergamon Press New York, First edition 1984, and "Comprehensive Heterocyclic Chemistry II, A Review of the Literature 1982–1995. The Structure, Reactions, Synthesis and Uses, of Heterocyclic Compounds" Katritzky, A. R., Rees, C. W. and Scriven, E., F. Eds Pergamon Press New York, 1996.

The compounds of the present invention may be prepared according to the following general synthetic schemes, as well as relevant published literature procedures that are used by one skilled in the art. Exemplary reagents and procedures for these reactions appear hereinafter and in the working Examples. Unless otherwise specified, the various substituents of the compounds are defined in the same manner as the formula I compound of the invention. The Schemes are particularly relevant to compounds in which J and K are carbon atoms.

Many of the reactions are conventional and their modification for adaptation for specific compounds of formula V or VIII (as in Scheme 1 & 2) would be known to one skilled in the art that the functionality present on the molecule should be consistent with the desired transformation and that modification of the order of the synthetic steps may be necessary to prepare a compound of the invention. Preferred method for the synthesis of Formula V compounds include but are not limited to, the methods described below.

Compounds claimed (V) in which M=N were synthesized as shown in Scheme 1, by sequential displacement of leaving groups on heterocycle I with appropriate amines, II and III in the presence of a base in appropriate solvent followed by the functionalization of the terminal amine with appropriate Z group. Examples of useful leaving groups, LG, on heterocycle I include but are not limited to Cl, Br, I, alkanesulfonate, arylsulfonate or perhaloalkanesulfonate. Useful bases include, but are not limited to, an excess of the amine itself (IV or II), metal carbonates such as $K_2CO_3$ or $CsCO_3$, hindered alkoxides such as potassium t-butoxide, or non-nucleophilic tertiary organic amines such as triethylamine, N,N-diisopropylethylamine or 4-methylmorpholine. Typical solvents include, but are not limited to, aprotic solvents such as NMP, DMF, dimethylacetamide, $CH_3CN$, dioxane, $CH_2Cl_2$, THF or protic solvents such as MeOH, EtOH, isopropanol, butanol, amyl alcohol, cyclohexanol and ethoxyethoxyethanol. The temperature range used for both steps in Scheme 1 is between −10° C. and 200° C. It is understood by one skilled in the art that mixtures of regioisomers of intermediate III may be obtained from the initial displacement reaction in Scheme 1. It is also understood by one skilled in the art that the regioisomers thus obtained can be separated and purified by recrystallization or column chromatography and then further reacted to give compounds of Formula V.

In a more detailed description of the procedure, one molar equivalent of an optionally substituted pyrimidine or pyridine (I)(synthesized as described in reference), such as 2,4 dichloro-pyrido[2,3-d]pyrimidine or 5,7-dichloro-[1,6] napthyridine or 2,4 dichloro-pyrido[3,2-d]pyrimidine or 2,4- dichloro-[1,8]napthyridine and one molar equivalent of a tertiary amine such as triethylamine, diisopropylethylamine or 4-methylmorpholine and one molar equivalent of an amine or alcohol or thiol, HLCHRPh(R1)n, are combined in a solvent such as 1,2-dichloroethane and maintained between −10° C. to 200° C. for a period of 1 to 48 hours. A preferred temperature range for this step is between 0° C. and 80° C. The reaction mixture can be filtered and the filtrate concentrated under reduced pressure to provide the intermediate product, III. Alternatively, the reaction mixture can be diluted with an organic solvent such as $CH_2Cl_2$ or EtOAc. The organic layer can then be washed with water and brine, dried over magnesium sulfate or sodium sulfate, filtered, and concentrated under reduced pressure to provide the intermediate product. The intermediate product may be purified by recrystallization or by chromatography on silica gel using an eluant such as EtOAc, hexanes, $CH_2Cl_2$, chloroform, $Et_2O$, MeOH, EtOH or mixtures thereof.

The second step of the synthesis consists of combining one molar equivalent of the intermediate product, III, with either two or more molar equivalents of amine, R4 MHCH2 (CH2)$_n$NR5PG, or one molar equivalent of amine, R4 MHCH2 (CH2)$_n$NR5PG, and one molar equivalent of a tertiary amine such as triethylamine, diisopropylethylamine, or 4-methylmorpholine, in a solvent such as NMP or ethoxyethoxyethanol for a period of 1 to 48 hours at reaction temperatures between −10° C. and 200° C. The reaction mixture is then allowed to cool to room temperature. The reaction mixture can be diluted with an organic solvent such as $CH_2Cl_2$ or EtOAc. The organic layer can then be washed with water and brine, dried over magnesium sulfate or sodium sulfate, filtered, and concentrated under reduced pressure to provide the intermediate product. The intermediate product may be purified by recrystallization or by chromatography on silica gel using an eluant such as EtOAc, hexanes, $CH_2Cl_2$, chloroform, $Et_2O$, MeOH, EtOH or mixtures thereof or used as such in the next step.

The third step of the synthesis consists of unmasking of protective group (PG) using acidic or catalytic hydrogenolysis or basic condition. The product was either purified using chromatographic methods or crystallized or used as such in the subsequent step.

The fourth step of the synthetic sequence consists of coupling of the terminal amine with one equivalent of Z using either a coupling reagent or a base. The preferred coupling agents are diisopropylcarbodiimide or N,N-diethylaminoethylcarbodiimide or dicyclohexylcarbodiimide in presence or absence of activator such as HOAt or HOBt. The preferred bases include triethylamine, diisopropylethylamine, or 4-methylmorpholine. The reaction mixture can be diluted with an organic solvent such as $CH_2Cl_2$ or EtOAc. The organic layer can then be washed with water and brine, dried over magnesium sulfate or sodium sulfate, filtered, and concentrated under reduced pressure to provide the intermediate product. The final product may be purified by recrystallization or by chromatography on silica gel using an eluant such as EtOAc, hexanes, $CH_2Cl_2$, chloroform, $Et_2O$, MeOH, EtOH or mixtures thereof or purified by reverse phase HPLC on C-18 using eluant such as MeOH, $CH_3CN$, $H_2O$, TFA or mixtures thereof.

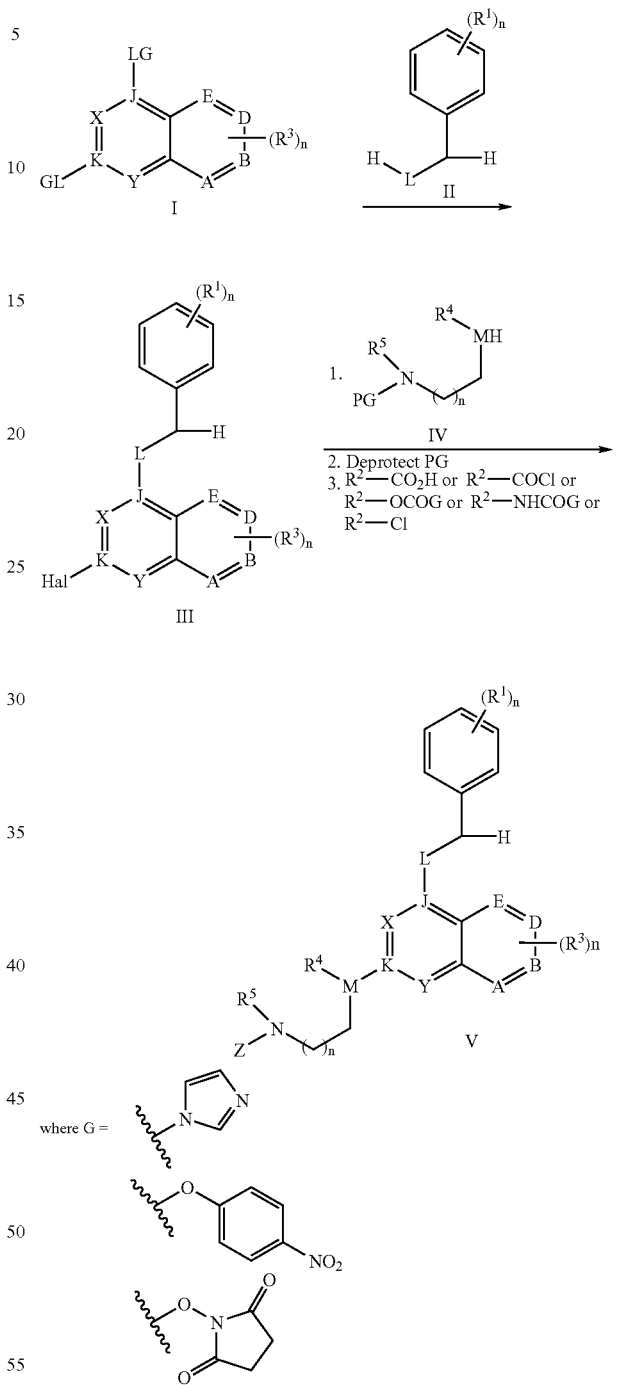

(Eur. J. Med. Chem, 24 (3), 209–16 (1989) and references cited therin)

Compounds claimed (VIII) in which M=C were synthesized as shown in Scheme 2, by displacement of leaving groups on suitably substituted heterocycle VI with appropriate amines, II in the presence of a base in appropriate solvent followed by the functionalization of the terminal amine with appropriate Z group. Examples of useful leaving groups, LG, on heterocycle I include but are not limited to Cl, Br, I, alkanesulfonate, arylsulfonate or perhaloalkanesulfonate. Useful bases include, but are not limited to, an excess of the amine itself (IV or II), metal carbonates such as $K_2CO_3$ or $CsCO_3$, hindered alkoxides such as potassium t-butoxide, or non-nucleophilic tertiary organic amines such as triethylamine, N, N-diisopropylethylamine or 4-methylmorpholine. Typical solvents include, but are not limited to, aprotic solvents such as NMP, DMF, dimethylacetamide, $CH_3CN$, dioxane, $CH_2Cl_2$, THF or protic solvents such as MeOH, EtOH, isopropanol, butanol, amyl alcohol, cyclohexanol and ethoxyethoxyethanol. The temperature range used for both steps in Scheme 1 is between –10° C. and 200° C.

In a more detailed description of the procedure, one molar equivalent of an optionally substituted pyrimidine or pyridine (VI), such as 4-chloro-pyrido[2,3-d]pyrimidine or 7-chloro-[1,6]napthyridine or 4-chloro-pyrido[3,2-d]pyrimidine or 4-chloro-[1,8]napthyridine (prepared by methods similar to as described in the references) and one molar equivalent of a tertiary amine such as triethylamine, diisopropylethylamine or 4-methylmorpholine and one molar equivalent of an amine or alcohol or thiol, HLCHRPh(R1)n, are combined in a solvent such as 1,2-dichloroethane and maintained between –10° C. to 200° C. for a period of 1 to 48 hours. A preferred temperature range for this step is between 0° C. and 80° C. The reaction mixture can be filtered and the filtrate concentrated under reduced pressure to provide the intermediate product, VII. Alternatively, the reaction mixture can be diluted with an organic solvent such as $CH_2Cl_2$ or EtOAc. The organic layer can then be washed with water and brine, dried over magnesium sulfate or sodium sulfate, filtered, and concentrated under reduced pressure to provide the intermediate product. The intermediate product may be purified by recrystallization or by chromatography on silica gel using an eluant such as EtOAc, hexanes, $CH_2Cl_2$, chloroform, $Et_2O$, MeOH, EtOH or mixtures thereof.

The second step of the synthesis consists of unmasking of protective group (PG) using acidic or catalytic hydrogenolysis or basic condition. The product was either purified using chromatographic methods or crystallized or used as such in the subsequent step.

The third step of the synthetic sequence consists of coupling of the terminal amine with one equivalent of Z using either a coupling reagent or a base. The preferred coupling agents are diisopropylcarbodiimide or N,N-diethylaminoethylcarbodiimide or dicyclohexylcarbodiimide in presence or absence of activator such as HOAt or HOBt. The preferred bases include triethylamine, diisopropylethylamine, or 4-methylmorpholine. The reaction mixture can be diluted with an organic solvent such as $CH_2Cl_2$ or EtOAc. The organic layer can then be washed with water and brine, dried over magnesium sulfate or sodium sulfate, filtered, and concentrated under reduced pressure to provide the intermediate product. The final product may be purified by recrystallization or by chromatography on silica gel using an eluant such as EtOAc, hexanes, $CH_2Cl_2$, chloroform, $Et_2O$, MeOH, EtOH or mixtures thereof or purified by reverse phase HPLC on C-18 using eluant such as MeOH, $CH_3CN$, $H_2O$, TFA or mixtures thereof.

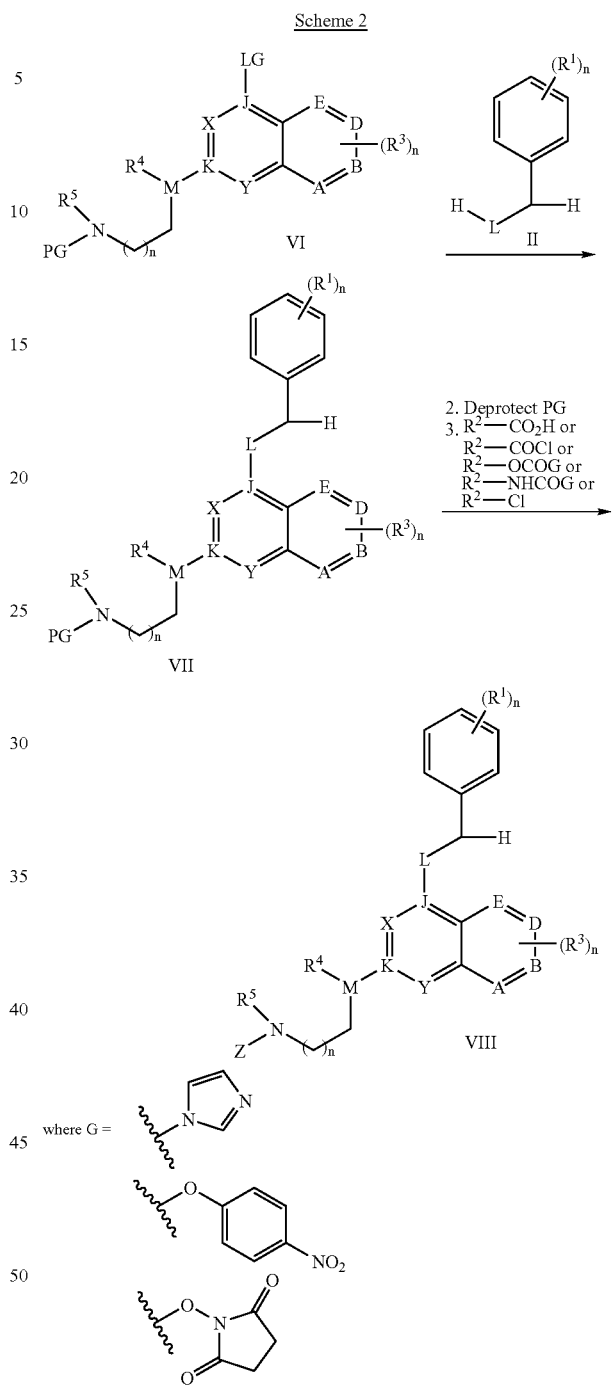

(Osselaere, J. P., *J. Pharm. Belg.*, (1974), 29(2), 145–51; Barlin, G. B.; Tan, W. L., *Aust. J. Chem.*, (1984), 37(5), 1065–73; Chandler, C. J., Deady, L. W., Reiss, J. A., Tzimos, V., *J. Heterocycl. Chem.* (1982), 19(5), 1017–19)

Utility

The chemokine receptor modulator compounds of formula I can be administered to animals, including man, to modulate chemokine receptor activity in vivo. Chemokine receptors are implicated as key mediators of inflammatory, infectious, and immunoregulatory disorders and diseases, including asthma, COPD, and allergic diseases; rheumatoid arthritis, atherosclerosis, and psoriasis; solid organ transplant rejection, osteoarthritis, and inflammatory bowel syndrome. Other therapeutic agents, such as those described below, may be employed with the inventive compounds in the present methods. In the methods of the present invention, such other therapeutic agent(s) may be administered prior to, simultaneously with or following the administration of the compound(s) of the present invention.

The compounds of the present invention can be used in treating a range of disorders exemplified by, but not limited to, diseases and conditions such as: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lungh diseases and the like, (9) autoimmune diseases, such as arthritis (including rheumatoid and psoriatic), multiple sclerosis, systemic lupus erythematosus, type I diabetes, glomerulonephritis, and the like, (10) graft rejection (including allograft rejection and graft-v-host disease), and (11) other diseases in which undesired inflammatory responses are to be inhibited (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout.

The present invention also provides pharmaceutical compositions comprising at least one of the compounds of formula I, or a salt thereof, capable of treating a CCR4 mediated condition or disease in an amount effective therefor, alone or in combination with at least one additional therapeutic agent, and any pharmaceutically acceptable carrier, adjuvant or vehicle. Additional therapeutic agents encompasses, but is not limited to, an agent or agents selected from the group consisting of an immunosuppressant, an anti-cancer agent, an anti-viral agent, an anti-inflammatory agent, an anti-fungal agent, an antibiotic, or an anti-vascular hyperproliferation compound.

The term "pharmaceutically acceptable carrier, adjuvant or vehicle" refers to a carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compounds of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.0001 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to CCR4-mediated conditions and diseases.

The compounds of the present invention may be employed alone or in combination with each other and/or other chemokine receptor modulators or other suitable therapeutic agents useful in the treatment of the aforementioned disorders including: Anti-diabetic agents; anti-osteoporosous agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phospodiesterase inhibitors; protein tyrosine kinase inhibitors; thyroid mimetics (including thyroid receptor antagonists); anabolic agents; HIV or AIDS therapies; therapies useful in the treatment of Alzheimer's disease and other cognitive disorders; therapies useful in the treatment of sleeping disorders; anti-proliferative agents; anti-tumor agents; and/or anti-ulcer and gastroesopheageal reflux disease agents.

Examples of suitable anti-diabetic agents for use in combination with the compounds of the present invention include biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 (attorney docket LA27), glucagon-like peptide-1 (GLP-1), and dipeptidyl peptidase IV (DP4) inhibitors.

Examples of suitable anti-osteoporosous agents for use in combination with the compounds of the present invention include alendronate, risedronate, raloxifene, calcitonin, non-steroidal progestin receptor agonists, RANK ligand agonists, calcium sensing receptor antagonists, TRAP inhibitors, selective estrogen receptor modulators (SERM), estrogen and AP-1 inhibitors;

Examples of suitable anti-obesity agents for use in combination with the compounds of the present invention include aP2 inhibitors such as those disclosed in U.S. Ser. No. 09/519,079 filed Mar. 6, 2000 (attorney docket LA27), PPAR gamma antagonists, PPAR delta agonists, and orlistat.

Examples of suitable antinflammatory agents for use in combination with the compounds of the present invention include prednisone, dexamethasone, Enbrel, cyclooxygenase inhibitors (i.e., COX-1 and/or COX-2 inhibitors such as NSAIDs, aspirin, indomethacin, ibuprofen, piroxicam, Naproxen, Celebrex, Vioxx), CTLA4-Ig agonists/antagonists, CD40 ligand antagonists, integrin antagonists, alpha4 beta7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., zelmac and Maxi-K openers such as those disclosed in U.S. Pat. No. 6,184,231 B1).

Examples of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors)(e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-COA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, choesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phospodiesterase inhibitiors for use in combination with the compounds of the present invention include PDEIII inhibitors such as cilostazol, and PDE V inhibitors such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone and SARMs.

Examples of suitable HIV or AIDS therapies for use in combination with the compounds of the present invention include indinavir sulfate, saquinavir, saquinavir mesylate, amprenavir, ritonavir, lopinavir, ritonavir/lopinavir combinations, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, taxol, FK 506, and adriamycin.

Examples of suitable anti-tumor agents for use in combination with the compounds of the present invention include taxol, adriamycin, epothilones, cisplatin and carboplatin.

The above other therapeutic agents, when employed in combination with the compounds of the present invention, may be used, for example, in those amounts indicated in the Physicians' Desk Reference (PDR) or as otherwise determined by one of ordinary skill in the art.

The utility of the compounds of the present invention as chemokine receptor modulators may be demonstrated by methodology known to those skilled in the art, such as the assays for CCR[12] and CCR3 ligand binding, as disclosed by Ponath, et al., *J. Exp. Med.* (1996), 183, 2437–2448, Uguccioni, et al., *J. Clin. Invest.* (1997), 100, 1137–1143, and White, et al., 2000, J. Biol. Chem. (2000), 275, 36626–36631. Cell lines that express the receptor of interest include those naturally expressing the receptor, or a cell engineered to express a recombinant chemokine receptor, such as CHO, HEK-293, or RBL.

The inventors used the following assay entitled "CEM BINDING ASSAY" to determine the degree of activity of the compounds disclosed herein as chemokine receptor modulators.

CEM Binding Assay

The cells used in this assay are CEM or CEMS529 or HEK-293/CCR4. For each filter plate, $1\times10^7$ Cells/ml are needed. See the examples below.

(a) 1 compound plate=2 filter plates=$1.1\times10^8$ cells resuspended in 11 ml (b) 2 compound plates=4 filter plates=$2.2\times10^8$ cells resuspended in 22 ml (c) ½ compound plate=1 filter plate=5.5 $10^7$ cells resuspended in 5.5 ml Procedure:
1. Prepare FILTER ASSAY BUFFER and warm in water bath. The FILTER ASSAY BUFFER consists of 0.5% BSA IN PBS (w/Mg and Ca).
2. Spin cells at 1100–1200 rpm for 8 minutes.
3. Aspirate off media.
4. Resuspend in 10 ml filter assay buffer, transfer to a 15 ml conical tube and spin 8 minutes at 1100–1200 rpm.
5. Aspirate off buffer.
6. Re-suspend in appropriate amount of filter assay buffer.
7. Bring prepared compound plates up to room temperature on bench top.
8. Block filters with 100 µl/well 0.03% PEI BLOCKING BUFFER which is made fresh daily in PBS (w/o Mg and Ca) from 10% PEI stock solution.
9. Incubate 15 minutes.
10. Wash plate #1 with 200 µl WASH BUFFER (PBS) once.
11. Wash plate #2 with 200 µl WASH BUFFER (PBS) once.
12. Wash plate #1 with WASH BUFFER (PBS) 3 times.
13. Add 39 µL FILTER ASSAY BUFFER to plate #1.
14. Wash plate #2 with WASH BUFFER (PBS) 3 times.
15. Add 39 µL FILTER ASSAY BUFFER to plate #2.
16. Add 1 µl of each drug concentration in duplicate.
17. Add 100% DMSO to the reagent control wells: columns 11–12, rows A–D. Tap the plates gently to mix
17. Add 50 µl of cells to each well
18. Add 1 µl of cold ligand (MDC or TARC) to non-specific binding wells columns 11–12, rows E–H. Add one extra µl of cold to H12 on plate #1.
19. Incubate 10 minutes @ room temperature, shake gently
20. Add 10 µl of hot ligand to each well. MDC or TARC must be at a concentration of 100 µC/ml in FILTER ASSAY BUFFER.
21. Cover and shake for 40 minutes
22. Incubate for 1 hour and 20 minutes after shaking stops.
23. Wash each plate 4 times with 200 µl of FILTER WASH BUFFER/well.

FILTER WASH BUFFER=0.25% NaCl+0.1% BSA+ PBS

24. Let filters dry 1–2 hours.
25. Add 25 µl of scintillation fluid to each well.
26. Cover and read plates in the Wallac Scintillation counter.

The biological activity of the compounds of the invention has been measured using the CEM binding assay described above. The range of activity measured was 5 nm to 100 µM. The compounds disclosed herein are capable of binding to chemokine receptors at a measurable level, using the above-described assay or an assay which can determine the binding activity to chemokine receptors.

The following Examples represent preferred embodiments of the invention, and are not intended to limit the scope of the present invention which is defined in the claims. All temperatures are in ° C. unless indicated otherwise.

Abbreviations employed in the Examples are defined below.

Abbreviations

| | |
|---|---|
| Ac | Acetyl |
| AcOH | Acetic acid |
| aq. | Aqueous |
| CDI | Carbonyldiimidazole |
| Bn | Benzyl |
| Boc | tert-butoxycarbonyl |
| DMAP | Dimethylaminopyridine |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| h | Hours |
| i | iso |
| HPLC | High pressure liquid chromatography |
| HOAc | Acetic acid |
| THF | Tetrahydrofuran |
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| $M^+$ | $(M + H)^+$ |
| $M^{+1}$ | $(M + H)^+$ |
| MS | Mass spectrometry |
| n | normal |
| Pd/C | Palladium on carbon |
| Ph | Phenyl |
| PPTS | Pyridinium p-toluenesulfonate |
| Pr | Propyl |
| p-TsOH | para-Toluenesulonic acid |
| Ret Time | Retention time |
| rt or RT | Room temperature |
| sat. | Saturated |
| TFA | Trifluoroacetic acid |
| THF | Tetrahydrofuran |
| TOSMIC | Tosylmethyl isocyanide |

EXAMPLE 1

Preparation of (R)-{4-[4-(2,4-Dichloro-benzylamino)-pyrido[2,3-d]pyrimidin-2-yl]-piperazin-1-yl}-piperidin-2-yl-methanone

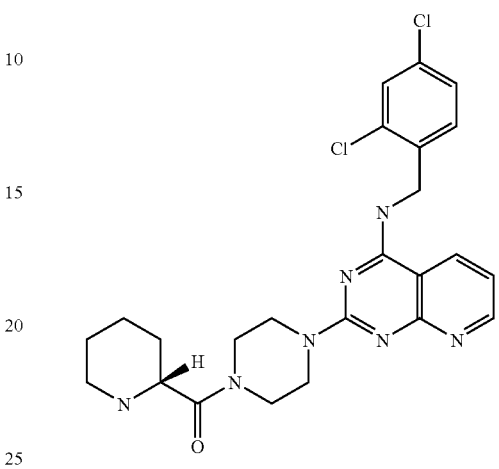

2,4-Dichlorobenzylamine (211 mg, 1.2 mmol) was added to the stirred solution of 2,4 dichloro-pyrido[2,3-d]pyrimidine(200 mg, 1 mmol) and N,N-diisopropylethylamine (266 μL, 1.5 mmol) in 1,2-dichloroethane (5 mL). The reaction mixture was stirred at room temperature for 12 h and then diluted with water (10 mL). The aqueous layer was extracted with $CH_2Cl_2$ and the combined organic layer was washed with water (2×10 mL), dried (Na2SO4) and concentrated in vaccuo to give (2-Chloro-pyrido[2,3-d]pyrimidin-4-yl)-(2,4-dichloro-benzyl)-amine as a yellow oil (185 mg) and was used as such in the next reaction without further purification.

Boc-piperazine (122 mg, 0.65 mmol) was added to the solution of (2-Chloro-pyrido[2,3-d]pyrimidin-4-yl)-(2,4-dichloro-benzyl)-amine(185 mg, 0.54 mmol) and N,N-diisopropylethylamine (145 μL, 0.82 mmol) in n-butanol (2 mL). The reaction mixture was stirred at 85° for 10 h. All starting material was consumed as seen on HPLC. The reaction mixture was concentrated at room temperature under vacuo. The resulting residue was suspended in 2 mL of TFA-CH2Cl2 (1:1) mixture and stirred at room temperature for 45 minutes. The reaction mixture was concentrated in vacuo, diluted with saturated aqueous sodium bicarbonate solution. The aqueous layer was extracted with CH2Cl2 (2×10 mL), dried (Na2SO4) and concentratd to furnish (2,4-Dichloro-benzyl)-(2-piperazin-1-yl-pyrido[2,3-d]pyrimidin-4-yl)-amine(210 mg) as pale brown oil. The crude was carried forward as such in the next reaction.

Boc-R-homoproline (50 mg, 0.21 mmol) was added to the solution of 2,4-Dichloro-benzyl)-(2-piperazin-1-yl-pyrido[2,3-d]pyrimidin-4-yl)-amine (70 mg, 0.18 mmol)and diisopropylcarbodiimide (27 mg, 0.21 mmol) in dichloromethane (2 mL). The reaction mixture was stirred at room temperature for 3 h whereupon complete disappearence of starting material was observed. To this solution was added a mixture (1 mL) of TFA-CH2Cl2 (1:1) and the resulting reaction mixture was stirred for additional 45 minutes. The reaction mixture was then concentrated in vacuo and purified by preparative HPLC (conditions below). The fractions were analyzed by LCMS. The desired fractions containing (R)-{4-[4-(2,4-Dichloro-benzylamino)-pyrido[2,3-d]pyrimidin- 2-yl]-piperazin-1-yl}-piperidin-2-yl-methanone were concentrated to give a pale brown oil (28 mg) as bis trifluoroacetic acid salt.

Preparative HPLC Condition: Column Shimadzu VP-ODS 20×100 mm; Flow Rate: 20 mL/min; Solvent A: Water:Methanol:TFA (90:9.9:0.1); Solvent B: Methanol:Water:TFA (90:9.9:0.1); Gradient: 30% B to 100% B (12 minutes); Retention time: 10.2 min.

$^1$H NMR (CDCl$_3$) δ 9.12 (d, 1H), 8.11 (d, 1H), 7.55 (dd, 1H), 7.26 (d, 1H), 7.17 (dd, 1H), 7.00 (d, 1H), 4.65 (s, 2H), 4.06 (m, 1H), 3.62–3.76 (m, 8H), 3.34–3.41 (m, 1H), 2.88–2.94 (m, 1H), 1.76–1.92 (m, 2H), 1.46–1.57 (m, 2H. MS (ESI$^+$)(M+H)$^+$ 500

Obviously, numerous modifications and variations of the present invention are possible in light of the above teachings. It is therefore to be understood that within the scope of the appended claims, the invention may be practiced otherwise than as specifically described herein.

What is claimed is:

1. A compound of formula (I)

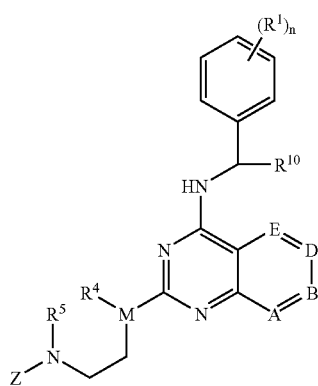

including enantiomers, diastereomers, tautomers, and pharmaceutically acceptable salts, thereof wherein:

A, B, D, and E, are selected from N or, and exactly one of A, B, D, and E is N;

M is CH or N;

Z is C(=O)GR$^2$ or C(H)$_2$GR$^2$;

G is O or NH or none, or when Z is C(=O)GR$^2$, G can also be alkylene;

n is 0–4;

R$^1$ is selected from halogen, —CN, —CF$_3$, substituted alkyl, aryl, and heteroaryl;

R$^2$ is a 5- to 6-membered heterocycloalkyl containing one N; and

R$^4$ and R$^5$ are H;

or R$^4$ and R$^5$ may be taken together with the atoms to which they are attached to form a ring wherein the ring is selected from piperidine and piperazine; and R$^{10}$ is selected from H, alkyl, substituted alkyl, alkenyl, and substituted alkenyl.

2. A compound of claim 1 including enantiomers, diastereomers, tautomers, and pharmaceutically acceptable salts, thereof wherein:

A is N;

B, D, and E are CH;

n is 2;

R$^1$ is selected from halogen, —CN, —CF$_3$, substituted alkyl, aryl, and heteroaryl; and R$^2$ is a piperidine or pyrrolidine ring.

3. A compound of claim 2 including enantiomers, diastereomers, tautomers, and pharmaceutically acceptable salts, thereof selected from:

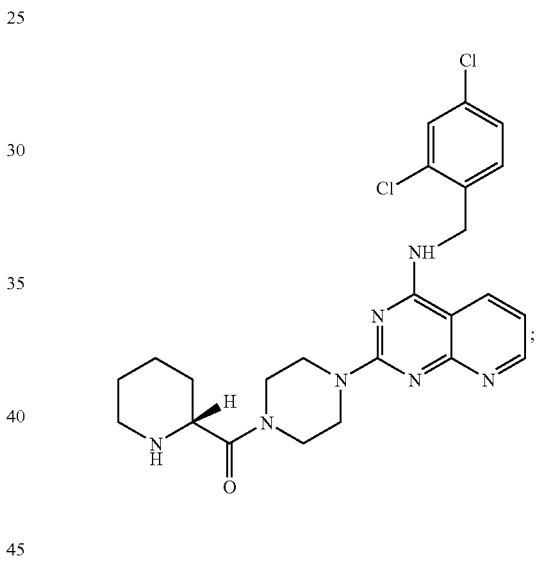

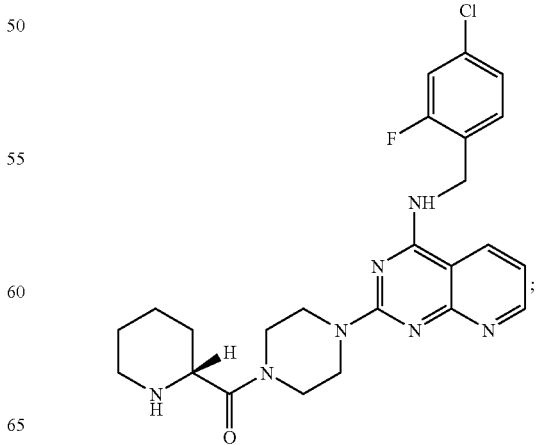

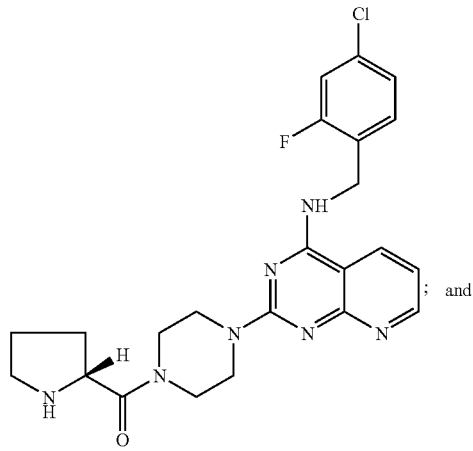
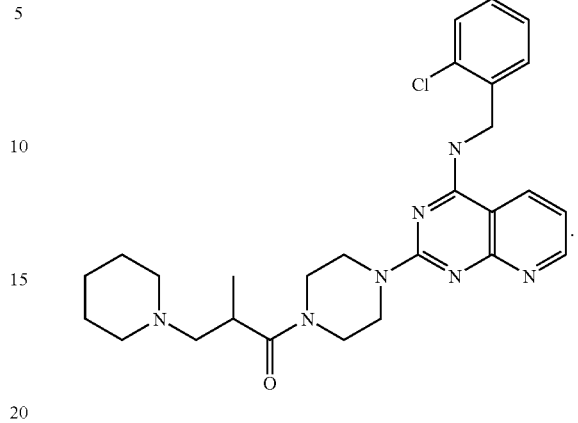
4. A pharmaceutical composition comprising a compound of claim 1 and a pharmaceutically acceptable carrier.
5. A method for the treatment of asthma in man comprising: administering a therapeutically effective amount of the pharmaceutical compound of claim 1.
* * * * *

UNITED STATES PATENT AND TRADEMARK OFFICE
CERTIFICATE OF CORRECTION

PATENT NO. : 7,202,249 B2  Page 1 of 1
APPLICATION NO. : 10/648677
DATED : April 10, 2007
INVENTOR(S) : Ashkok V. Purandare It is certified that error appears in the above-identified patent and that said Letters Patent is hereby corrected as shown below:

In the Claims:

Col. 27, line 54, change "N or," to -- N or C, --.

Signed and Sealed this

Fifteenth Day of July, 2008

JON W. DUDAS
*Director of the United States Patent and Trademark Office*